United States Patent
Joe et al.

(10) Patent No.: US 10,227,637 B2
(45) Date of Patent: Mar. 12, 2019

(54) MELTING CURVE ANALYSIS USING PNA PROBE, METHOD AND KIT FOR ANALYZING NUCLEOTIDE POLYMORPHISM USING MELTING CURVE ANALYSIS

(71) Applicant: PANAGENE INC., Daejeon (KR)

(72) Inventors: Goon Ho Joe, Daejeon (KR); Sung-Kee Kim, Daejeon (KR); Heekyung Park, Daejeon (KR); Chwang Siek Park, Daejeon (KR); Se Ryun Kim, Daejeon (KR); Yongtae Kim, Sejong (KR); Su Nam Kim, Gyeongsangnam-do (KR)

(73) Assignee: PANAGENE INC., Daejeon (KR)

( * ) Notice: Subject to any disclaimer, the term of this patent is extended or adjusted under 35 U.S.C. 154(b) by 52 days.

(21) Appl. No.: 15/300,771

(22) PCT Filed: Apr. 4, 2014

(86) PCT No.: PCT/KR2014/002909
§ 371 (c)(1),
(2) Date: Sep. 29, 2016

(87) PCT Pub. No.: WO2015/152446
PCT Pub. Date: Oct. 8, 2015

(65) Prior Publication Data
US 2017/0067092 A1    Mar. 9, 2017

(51) Int. Cl.
*C12Q 1/68*     (2018.01)
*C12Q 1/6818*   (2018.01)

(52) U.S. Cl.
CPC .................. *C12Q 1/6818* (2013.01)

(58) Field of Classification Search
CPC .................. C12Q 1/68; C07H 21/00
See application file for complete search history.

(56) References Cited

U.S. PATENT DOCUMENTS

| 6,355,421 | B1 | 3/2002 | Coull et al. | |
| 6,485,901 | B1 * | 11/2002 | Gildea ................ | C07K 14/003 435/5 |
| 2008/0176226 | A1 | 7/2008 | Chiou et al. | |
| 2014/0017685 | A1 | 1/2014 | Fu | |

FOREIGN PATENT DOCUMENTS

| JP | 2005-338024 | | 12/2005 |
| WO | 2007018734 | A2 | 2/2007 |
| WO | 2013009070 | A2 | 1/2013 |
| WO | WO2013009070 | * | 1/2013 |

OTHER PUBLICATIONS

Miyake et al., Sensitive detection of FGFR3 mutations in bladder cancer and urine sediments by peptide nucleic acid-mediated real-time PCR clamping. BBRC 362 : 865 (Year: 2007).*
Ortiz et al., PNA molecular beacons for rapid detection of PCR annplicons . Molecular and Cellular Probes 12 : 219 (1998) (Year: 1998).*
Seitz, O. Agnew. Chem. Int. Ed. 39 (18) 3249 (2000) (Year: 2000).*
Stratagene Catalog p. 39 (Year: 1988).*
Kuhn et al., JACS 124(6) : 1097 (Year: 2002).*
Beau-Faller, M., et al., "Detection of K-Ras Mutations in Tumour Samples of Patients with Non-Small Cell Lung Cancer Using PNA-mediated PCR Clamping", "British Journal of Cancer", Jan. 12, 2009, pp. 985-992, vol. 100.
Chen, C., et al., "Rapid Detection of K-ras Mutations in Bile by Peptide Nucleic Acid-mediated PCR Clamping and Melting Curve Analysis: Comparison with Restriction Fragment Length Polymorphism Analysis", "Molecular Diagnostics and Genetics", 2004, pp. 481-489, vol. 50, No. 3.
Dueholm, K., et al., "Synthesis of Peptide Nucleic Acid Monomers Containing the Four Natural Nucleobases: Thymine, Cytosine, Adenine, and Guanine and Their Oligomerization", "The Journal of Organic Chemistry", Mar. 28, 1994, pp. 5767-5773, vol. 59, No. 19.
Hladnik, U., et al., "Single-tube Genotyping of MBL-2 Polymorphisms Using Melting Temperature Analysis", "Clinical and Experimental Medicine", May 24, 2002, pp. 105-108, vol. 2.
Oh, J., et al., "Detection of Low-Level KRAS Mutations Using PNA-Mediated Asymmetric PCR Clamping and Melting Curve Analysis with Unlabeled Probes", "Journal of Molecular Diagnostics", Jul. 2010, pp. 418-424, vol. 12, No. 4.
Ririe, K., et al., "Product Differentiation by Analysis of DNA Melting Curves during the Polymerase Chain Reaction", "Analytical Biochemistry", 1997, pp. 154-160, vol. 245.
Sasaki, H., et al., "EGFRMutation Status inJapanese Lung Cancer Patients: Genotyping Analysis Using LightCycler", "Clinical Cancer Research", Apr. 15, 2005, pp. 2924-2929, vol. 11, No. 8.

(Continued)

*Primary Examiner* — Ethan C Whisenant
(74) *Attorney, Agent, or Firm* — Hultquist, PLLC; Steven J. Hultquist (57) ABSTRACT

Provided are a PNA probe for detecting nucleotide polymorphism of a target gene, a melting curve analysis method for detecting the nucleotide polymorphism of the target gene using the same, a nucleotide polymorphism analysis method of a target gene including the melting curve analysis method, and a kit for detecting the nucleotide polymorphism of the target gene containing the PNA probe. It is characterized that the PNA probe according to the present invention contains negative charge molecules. The modified PNA probe according to the present invention contains the negative charge molecules to have a high recognition ability with respect to a target DNA and a high coupling ability to the target DNA and to be rapidly dissociated by heat, such that the nucleotide polymorphism analysis may be relatively easily performed even in a heterozygous sample showing two melting curve graphs, and two or more adjacent single nucleotide polymorphisms may be simultaneously analyzed.

7 Claims, 6 Drawing Sheets
Specification includes a Sequence Listing.

(56) References Cited

OTHER PUBLICATIONS

Thomson, S., et al., "Fmoc Mediated Synthesis of Peptide Nucleic Acids", "Tetrahedron", Apr. 6, 1995, pp. 6179-6194, vol. 51, No. 22.

Zhang, M., et al., "Rapid Detection of Hepatitis B Virus Mutations Using Real-Time PCR and Melting Curve Analysis", "Heptology", Sep. 2002, pp. 723-728, vol. 36, No. 3.

Silvester, N., et al., "Effect of terminal amino acids on the stability and specifically of PNA-DNA hybridisation", "Organic & Biomolecular Chemistry", Nov. 1, 2007, pp. 917-923, vol. 5, No. 6, Publisher: www.rsc.org/obc.

\* cited by examiner

MELTING CURVE ANALYSIS USING PNA PROBE, METHOD AND KIT FOR ANALYZING NUCLEOTIDE POLYMORPHISM USING MELTING CURVE ANALYSIS

TECHNICAL FIELD

The present invention relates to a modified PNA probe for detecting nucleotide polymorphism of a target gene, a melting curve analysis method using a PNA probe comprising a reporter and a quencher coupled thereto, a method of analyzing the nucleotide polymorphism of the target gene using the same, and a kit for detecting the nucleotide polymorphism of the target gene containing the PNA probe, and more specifically, to a melting curve analysis method using a PNA probe, a nucleotide polymorphism analysis method through a melting curve analysis, and a nucleotide polymorphism analysis kit, wherein the PNA probe contains negative charge molecules.

BACKGROUND ART

A single nucleotide polymorphism (SNP), which is a genetic variation caused by substitution of one nucleotide in DNA nucleotides, brings individual difference for each person on a cause of disease, reaction to a therapeutic agent, and the like. Attention has been focused on detection and confirmation of the SNP since they are connected to new drug development as well as personalized medicine.

In order to rapidly detect the SNP, various detecting methods in which a real-time PCR technology is applied have been used. As a representative example of the various detecting methods, there are an analysis method using DNA intercalating fluorescent material, a method of using a DNA probe, a method of using a PNA probe, and the like.

A single nucleotide polymorphism analysis method using DNA intercalating fluorescent material may differentiate a change in nucleotide of PCR amplicon by a saturation concentration of the DNA intercalating fluorescent material without additional operation with respect to a product obtained after performing a PCR reaction. However, the method has a limitation in using the DNA intercalating fluorescent material, and has disadvantages in that the only one single nucleotide is capable of being analyzed and a program for analyzing a melting curve should be used [Kirk M. Ririe, et al., *ANALYTICAL BIOCHEMISTRY* 245: 154160, 1997; U. Hladnik et al., *Clin Exp Med* 2:105108, 2002].

As the DNA probe used for the melting curve analysis, there are an MGB Taqman probe, a Molecular Beacon (MB) probe, and a binary probe. The above-listed methods have an advantage in that an excellent differentiable ability of the SNP is shown, but have a disadvantage in that it is difficult to detect the adjacent SNPs by one reaction because the minimum length of the DNA probe is long to be about 20-40 mer [Hidefumi Sasaki et al., *Clin Cancer Res* 11:2924-2929, 2005; Manna Zhang et al., *HEPATOLOGY* 36:3, 2002].

A melting curve analysis method using a PNA probe characterized by containing negative charge molecules has advantages in that the PNA probe is capable of rapidly and strongly coupling to a target DNA as compared to the existing PNA probe, and due to the strong coupling ability, a probe having a short length is capable of being used, such that adjacent single nucleotide polymorphism is capable of being detected.

RELATED ART DOCUMENT

Non-Patent Document (Non-Patent Document 1) Chen, C. Y., et al., *Clin. Chem* 50:481-489, 2004
(Non-Patent Document 2) M Beau-Faller et al., *British Journal of Cancer* 100:985-992, 2009

SUMMARY

An object of the present invention is to provide a PNA probe capable of detecting nucleotide polymorphism of a target gene. In particular, it is characterized that the PNA probe contains negative charge molecules.

Another object of the present invention is to provide a melting curve analysis method for detecting the nucleotide polymorphism of the target gene using the PNA probe and a nucleotide polymorphism analysis method including the same.

Another object of the present invention is to provide a kit for detecting the nucleotide polymorphism of the target gene containing the PNA probe.

DESCRIPTION OF DRAWINGS

FIG. 2 shows a melting curve graph obtained by coupling a PNA probe to a heterozygous sample having a single nucleotide polymorphism;
 (a) a case of using a sample containing a non-modified PNA probe and DNA oligomers of SEQ ID NOs: 10 and 11 in Table 2 mixed at a ratio of 1:1.
 (b) a case of using a sample containing a PNA probe coupled to γ-glutamic acid and DNA oligomers of SEQ ID NOs: 10 and 11 in Table 2 mixed at a ratio of 1:1.
 (c) a case of using a sample containing a non-modified PNA probe and DNA oligomers of SEQ ID NOs: 10 and 12 in Table 2 mixed at a ratio of 1:1.
 (d) a case of using a sample containing a PNA probe coupled to γ-glutamic acid and DNA oligomers of SEQ ID NOs: 10 and 12 in Table 2 mixed at a ratio of 1:1.
 (e) a case of using a sample containing a non-modified PNA probe and DNA oligomers of SEQ ID NOs: 10 and 13 in Table 2 mixed at a ratio of 1:1.
 (f) a case of using a sample containing a PNA probe coupled to γ-glutamic acid and DNA oligomers of SEQ ID NOs: 10 and 13 in Table 2 mixed at a ratio of 1:1.
FIG. 4 shows a multiplex detection using three PNA probes to which γ-glutamic acids are coupled; a black line indicates a melting curve by a PNA probe of SEQ ID NO:

2, a blue line indicates a melting curve by a PNA probe of SEQ ID NO: 7, and a red line indicates a melting curve by a PNA probe of SEQ ID NO: 8.
(a) a case of an experiment with homozygous samples consisting of three PNA probes comprising γ-glutamic acids coupled thereto and target DNA oligomers complementary-binding to each probe.
(b) a case of an experiment with homozygous samples consisting of three PNA probes comprising γ-glutamic acids coupled thereto and target DNA oligomers mismatching to each probe due to single nucleotide polymorphism.
(c) a case of an experiment using heterozygous samples containing of three PNA probes comprising γ-glutamic acids coupled thereto and the target DNA oligomers used in (a) and (b) above mixed with each other at a ratio of 1:1.

FIG. 6 shows a melting curve graph obtained by coupling the PNA probe to various heterozygous samples having a single nucleotide polymorphism;
(a) a case of using a sample containing a PNA probe of SEQ ID NO: 9 in Table 1 and DNA oligomers of SEQ ID NOs: 21 and 22 in Table 2 mixed with each other at a ratio of 1:1.
(b) a case of using a sample containing a PNA probe of SEQ ID NO: 9 in Table 1 and DNA oligomers of SEQ ID NOs: 25 and 26 in Table 2 mixed with each other at a ratio of 1:1.
(c) a case of using a sample containing a PNA probe of SEQ ID NO: 9 in Table 1 and DNA oligomers of SEQ ID NOs: 21 and 23 in Table 2 mixed with each other at a ratio of 1:1.
(d) a case of using a sample containing a PNA probe of SEQ ID NO: 9 in Table 1 and DNA oligomers of SEQ ID NOs: 25 and 27 in Table 2 mixed with each other at a ratio of 1:1.
(e) a case of using a sample containing a PNA probe of SEQ ID NO: 9 in Table 1 and DNA oligomers of SEQ ID NOs: 21 and 24 in Table 2 mixed with each other at a ratio of 1:1.
(f) a case of using a sample containing a PNA probe of SEQ ID NO: 9 in Table 1 and DNA oligomers of SEQ ID NOs: 25 and 28 in Table 2 mixed with each other at a ratio of 1:1.

DETAILED DESCRIPTION OF THE INVENTION

The present invention provides a PNA probe comprising a reporter and a quencher coupled thereto for detecting nucleotide polymorphism of a target gene.

It is characterized that the PNA probe contains negative charge molecules, wherein the negative charge molecule may be at least one selected from a group consisting of all acids including amino acids, amino acid side chains, phosphoric acids, carboxylic acids, sulfonic acids, nitric acids and boric acids.

In addition, the negative charge molecule may be coupled to an N terminal, a C terminal of the PNA probe, or alpha, beta or gamma position of a PNA backbone, and at least one negative charge molecule may be consecutively or intermittently coupled to a base of the probe.

The present invention provides a melting curve analysis method using the PNA probe comprising the reporter and the quencher coupled thereto.

It is characterized that the PNA probe used in the melting curve analysis method contains negative charge molecules, and due to the use of the PNA probe containing negative charge molecules, resolution of the melting curve is increased, such that it is easy to analyze a heterozygous sample.

The PNA probe containing negative charge molecules according to the present invention may contain at least one negative charge molecules selected from a group consisting of all acids including amino acids, amino acid side chains, phosphoric acids, carboxylic acids, sulfonic acids, nitric acids and boric acids. The negative charge molecule may be coupled to an N terminal, a C terminal of the PNA probe, or alpha, beta or gamma position of a PNA backbone, and at least one negative charge molecule may be consecutively or intermittently coupled to a base of the probe.

In addition, the PNA probe may contain a fluorescent material. The fluorescent material may be a reporter, a quencher, or an intercalating fluorescent material.

The present invention provides a nucleotide polymorphism analysis method of a target gene using the PNA probe containing negative charge molecules.

The nucleotide polymorphism analysis method of a target gene may be used by analyzing the melting curve.

Figure 1:
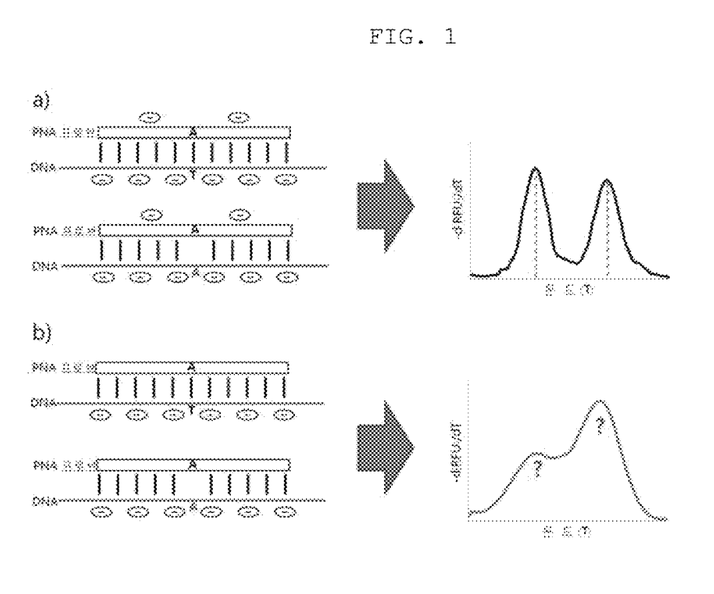
FIG. 1 is a schematic view showing a PNA probe coupled to a target DNA and a melting curve graph;
 (a) a case of using a PNA probe coupled to a side chain of an amino acid having negative charges.
 (b) a case of using a non-modified PNA probe.

Since the PNA has excellent thermal stability and biological stability, and high recognition ability with respect to a target DNA and high coupling ability to the target DNA as compared to DNA, the PNA may be used as a probe of a real-time PCR technology for detecting single nucleotide polymorphism (SNP). However, since the real-time PCR method uses the fluorescent material in detecting the target DNA in a sample, in order to detect the SNP at one position, there is a problem in that a probe having two fluorescent materials having different wavelengths is needed. The above-mentioned problem is a significant limitation in conducting a multiplex detection, and the present invention may solve the problem through the melting curve analysis of the fluorescent probe. However, in the case where the melting curve analysis is conducted using a non-modified PNA probe, since a half width at half maximum of a melting curve graph is large, there is a disadvantage in that an analysis result with the heterozygous sample is not precise. Accordingly, the present inventors tried to couple the backbone of the PNA probe to a side chain of an amino acid having negative charges, such that as temperature becomes increased, the PNA probe and the target DNA are rapidly dissociated, thereby making it possible to precisely analyze the melting curve. The simplified schematic view therefore was shown in FIG. 1.

The PNA probe according to the present invention may be applied to various molecule diagnostic technologies such as the following examples due to a small half width at halt maximum of the melting curve graph. For example, in a case where nucleotide polymorphism occurs in codons at various positions in a short nucleotide sequence, since resolution of the melting curve is high, whether the nucleotide polymorphism occurred at one position or at two or various positions, may be detected using one PNA probe. In addition, due to the high resolution, the melting curve may be differentiated according to a base at position at which the nucleotide polymorphism occurred, and thus, nucleotide sequence having modification may be simply figured out without a separate analysis such as a sequencing analysis.

The melting curve analysis method for detecting the nucleotide polymorphism using the PNA probe according to the present invention may enable to conduct the multiplex detection of nucleotide polymorphism due to the increased resolution of the melting curve, and in addition, even in a case where the SNPs are adjacent to each other, the multiplex detection may be conducted.

Further, even a case where a base forming a mismatch at a different position rather than the SNP modified position of the target DNA as well as the PNA probe to which the side chain of the amino acid having negative charges is coupled according to the present invention is introduced, may obtain an effect similar to that of the above-described case.

The present invention provides a nucleotide polymorphism analysis method of a target DNA comprising:
isolating a target DNA from a testing sample;
hybridizing the target DNA with a PNA probe comprising a reporter and a quencher coupled thereto;
obtaining a melting curve by melting a product obtained by the hybridization while changing a temperature; and
analyzing the obtained melting curve.

It is characterized that the PNA probe used in the nucleotide polymorphism analysis method of the target gene, and the melting curve analysis method contains negative charge molecules, wherein the PNA probe containing the negative charge molecules may contain at least one negative charge molecules selected from a group consisting of all acids including amino acids, amino acid side chains, phosphoric acids, carboxylic acids, sulfonic acids, nitric acids and boric acids. The negative charge molecule may be coupled to an N terminal, a C terminal of the PNA probe, or alpha, beta or gamma position of a PNA backbone, and at least one negative charge molecule may be consecutively or intermittently coupled to each base of the PNA probe.

In addition, the PNA probe used in the nucleotide polymorphism analysis method and the melting curve analysis method according to the present invention may contain a fluorescent material. The probe may have the reporter and the fluorescent material of the quencher capable of quenching fluorescence of the reporter coupled to both end thereof, and may contain an intercalating fluorescent material. The reporter may be at least one selected from a group consisting of FAM(6-carboxyfluorescein), Texas red, JOE, TAMRA, CY5 and CY3, and the quencher is preferably TAMRA(6-carboxytetramethyl-rhodamine), BHQ1, BHQ2, or Dabysyl, but the present invention is not limited thereto. The intercalating fluorescent material may be selected from a group consisting of acridine homodimer and derivatives thereof, acridine orange and derivatives thereof, 7-aminoactinomycin D (7-AAD) and derivatives thereof, actinomycin D and derivatives thereof, 9-amino-6-chloro-2-methoxyacridine (ACMA) and derivatives thereof, DAPI and derivatives thereof, dihydroethidium and derivatives thereof, ethidium bromide and derivatives thereof, ethidium homodimer-1 (EthD-1) and derivatives thereof, ethidium homodimer-2 (EthD-2) and derivatives thereof, ethidium monoazide and derivatives thereof, hexidium iodide and derivatives thereof, bisbenzimide, Hoechst 33258 and derivatives thereof, Hoechst 33342 and derivatives thereof, Hoechst 34580 and derivatives thereof, hydroxystilbamidine and derivatives thereof, LDS 751 and derivatives thereof, propidium Iodide (PI) and derivatives thereof and Cy-dyes derivatives.

The PNA probe contains the negative charge molecules coupled thereto used in the nucleotide polymorphism analysis method of the target gene may contain the reporter and the quencher. The PNA probe containing the negative charge molecules, the reporter, and the quencher is hybridized with the target DNA and then a fluorescent signal is generated, and as a temperature becomes increased, the PNA probe and the target DNA are rapidly melted at an optimum melting temperature of the probe due to a negative charge effect, such that the fluorescent signal is quenched. As compared to a PNA probe without negative charges, the PNA probe containing the negative charges is rapidly dissociated from the target DNA to increase resolution of the melting curve. Through the melting curve analysis having the high resolution obtained from the fluorescent signal according to a change in temperature, nucleotide polymorphism of the target DNA may be analyzed.

In addition, the PNA probe contains the negative charge molecules coupled thereto used in the nucleotide polymorphism of the target gene may contain an intercalating fluorescent material. The probe contains the negative charge molecules and the intercalating fluorescent material coupled thereto is hybridized with the target DNA and then a fluorescent signal is generated, and due to a negative charge effect, the PNA probe and the target DNA are rapidly melted at an optimum melting temperature of the probe, such that the fluorescent signal is quenched. Through the melting curve analysis having the high resolution obtained according to temperature of the fluorescent signal, nucleotide polymorphism of the target DNA may be analyzed.

Further, the nucleotide polymorphism analysis method of the target gene according to the present invention may include analyzing the melting curve obtained by using the detection of the fluorescent signal without a direct coupling of the intercalating fluorescent material to the probe.

The present invention provides a kit for analyzing the nucleotide polymorphism of the target gene using the melting curve analysis method of the PNA probe comprising the reporter and the quencher coupled thereto.

It is characterized that the PNA probe contains negative charges, and the kit preferably contains the PNA probe comprising the reporter and the quencher coupled thereto, but the present invention is not limited thereto.

The kit for analyzing the nucleotide polymorphism may be used by analyzing nucleotide polymorphism of a multiplex target DNA or a single target DNA.

Hereinafter, the present invention will be described in detail with reference to the following Examples. These examples are only for exemplifying the present invention, and it will be obvious to those skilled in the art that the scope of the present invention is not construed to be limited to these examples according to the gist of the present invention.

Example 1 PNA Probe Used in Melting Curve Analysis Experiment, Target DNA Oligomer Synthesis, and Melting Curve Analysis Method In order to perform a melting curve analysis of the present invention, PNA probes shown as the following Table 1 were synthesized to be used.

TABLE 1

Sequence of PNA Probe Used in Present Invention

| SEQ ID NO. | Name | Sequence (N' -> C') | Length of Sequence |
|---|---|---|---|
| 1 | 861-F71 | Dabcyl-CAAACAGCTGGG-OK-ROX | 12 |
| 2 | 861-glu2-71-65 | Dabcyl-CAAACAGCTGGG-OK-ROX | 12 |
| 3 | 858-F-78 | Dabcyl-TTGGGCGGGCC-OK-ROX | 11 |
| 4 | 858-glu2-70 | Dabcyl-TTGGGCGGCC-OK-ROX | 11 |
| 5 | 858-glu270 | Dabcyl-TTGGGCGGGCC-OK-ROX | 11 |
| 6 | 858-glu-270 | Dabcyl-TTGGGCGGGCC-OK-ROX | 11 |
| 7 | 18-2-3 | Dabcyl-TAGTTGGGATGTAC-OK-FAM | 14 |
| 8 | K13_melt | Dabcyl-ACGCCACCAGCTCC-OK-HEX | 14 |
| 9 | K | Dabcyl-GAGCTTGGTGGCG-OK-FAM | 13 |

In Table 1 above, O indicates a linker, a bold letter indicates γ-glutamic acid-PNA monomer and K indicates lysine.

The PNA probe was prepared by synthesizing a PNA oligomer from a benzothiazolesulfonyl (Bts) group-protected PNA monomer and a functionalized resin by a solid phase synthesis according to a method described in Korean Patent Publication No. 464261 [Lee et al., *Org. Lett.,* 9:3291-3293, 2007]. In addition to the above-described method, the PNA probe may be synthesized using a 9-flourenylmethloxycarbonyl (Fmoc) or tbutoxycarbonyl (t-Boc) synthesis method [Kim L. et al., *J. Org. Chem.* 59:5767-5773, 1994; Stephen A. et al., *Tetrahedron,* 51:6179-6194, 1995]. The reporter material and the quencher material were labeled on the PNA probe according to a widely known method in the art.

As a target DNA oligomer to be coupled to the PNA probe, a DNA oligomer synthesized by Bioneer Corporation (Korea) was used.

TABLE 2

Sequence of DNA Oligomer used in Present Invention

| SEQ ID NO. | Name | Sequence (5' -> 3') | Length of Sequence |
|---|---|---|---|
| 10 | 58T-61T | CGCACCCAGCTGTTTGGCCTGCCCAAAATC | 30 |
| 11 | 58T-61A | CGCACCCAGCAGTTTGGCCTGCCCAAAATC | 30 |
| 12 | 58T-61G | CGCACCCAGCGGTTTGGCCTGCCCAAAATC | 30 |
| 13 | 58C-61C | CGCACCCAGCCGTTTGGCCTGCCCAAAATC | 30 |
| 14 | 58A-61C | CGCACCCAGCCGTTTGGCCAGCCCAAAATC | 30 |
| 15 | Tm-13-04 | CATGTACGTCCCAACTACATG | 21 |
| 16 | Tm-13-01 | CATGTACGTCACAACTACATG | 21 |
| 17 | 2120758-G(W) | AAGGTTGGAGATGGTGGCGTAGGCTA | 26 |
| 18 | 2120758-C | AAGGTTGGAGATGCTGGCGTAGGCTA | 26 |
| 19 | 3Target_W | CACCCAGCTGTTTGGAAGCATGGTACGCCACTAAGCTCCAAGGAATCGGTTGGAGATGGTGGCGTAGGCTA | 71 |
| 20 | 3Target_M | CACCCAGCAGTTTGGAAGCATGGTACGCCAGTAAGCTCCAAGGAATCGGTTGGAGATGCTGGCGTAGGCTA | 71 |
| 21 | K(D) | CATGCGCCACCAAGCTCCATG | 21 |
| 22 | K(D)-0A | CATGCGCCACTAAGCTCCATG | 21 |
| 23 | K(D)-0C | CATGCGCCACGAAGCTCCATG | 21 |
| 24 | K(D)-0T | CATGCGCCACAAAGCTCCATG | 21 |
| 25 | K(D)-0A | CATGCGCCACTAAGCTCCATG | 21 |
| 26 | K(D)-1A | CATGCGCCAATAAGCTCCATG | 21 |
| 27 | K(D)-2A | CATGCGCCAGTAAGCTCCATG | 21 |
| 28 | K(D)-3A | CATGCGCCATTAAGCTCCATG | 21 |

1.25 μM of PNA probes listed in Table 1 above, 0.25 μM of DNA oligomers listed in Table 2 above, and PCR amplification solution (Enzynomics Co., Ltd., Korea) were added and mixed with each other, followed by reaction at 95° C. for 5 minutes using real-time PCR machine (CFX96™ Real-time PCR System), temperature was decreased at a rate of 0.1° C./sec until 40° C. and the reactant was maintained for five minutes, and then fluorescence was measured while increasing temperature by 0.5° C. from 40° C. up to 95° C. thereby conducting the melting curve analysis.

Figure 2:
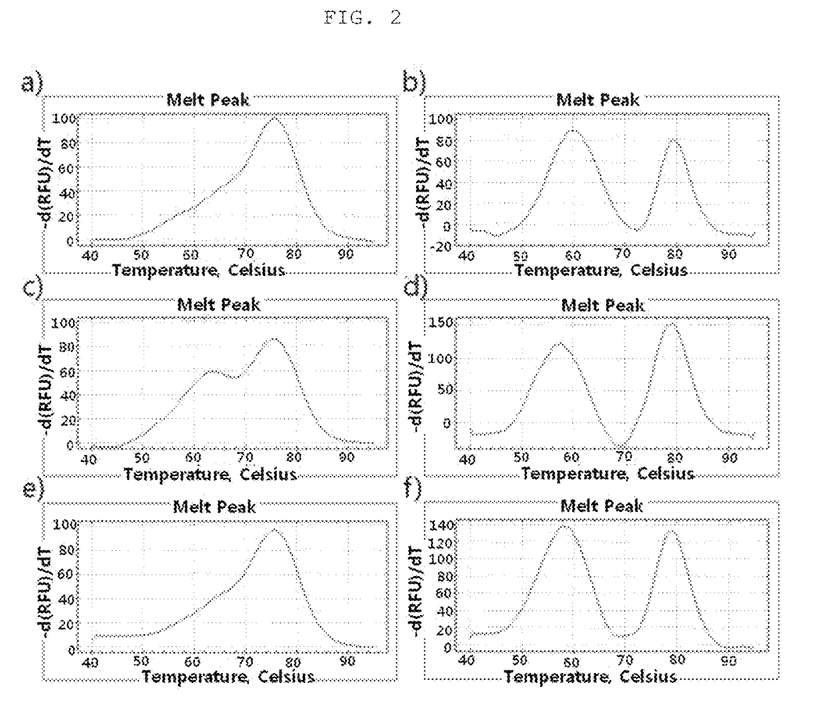

Example 2 Melting Curve Analysis of Heterozygous Sample Having Single Nucleotide Polymorphism Using PNA Probe Comprising γ-Glutamic Acid Coupled Thereto In order to compare a difference in melting curves between PNA probe comprising γ-glutamic acid coupled thereto and a non-modified PNA probe, melting curves were analyzed by experiment using samples containing PNA probes of SEQ ID NOs: 1 and 2 in Table 1 and oligomers prepared by mixing a DNA oligomer of SEQ ID NO: 10 in Table 2 with one of DNA oligomers of SEQ ID NOs: 11 to 13 in Table 2 at a ratio of 1:1, by the method of Example 1 above, respectively.

Results thereof were shown in FIG. 2. It could be appreciated that in a case where the PNA probe comprising γ-glutamic acid coupled thereto, that is, the PNA probe contains negative charge molecules introduced thereinto was used, due to an negative charge effect, the PNA probe was rapidly dissociated from the target DNA according to an increase in temperature, such that resolution of the melting curve in a heterozygous sample having SNP was remarkably increased.

Example 3 Melting Curve Analysis of Heterozygous Sample Having Single Nucleotide Polymorphism According to Position of γ-Glutamic Acid Coupled to PNA Probe In order to compare a difference in melting curves according to a position of γ-glutamic acid which is negative charge molecules coupled to the PNA probe, melting curves were analyzed by experiment using samples containing PNA probes of SEQ ID NOs: 3, 4, 5, and 6 in Table 1 and DNA oligomers of SEQ ID NOs: 13 to 14 in Table 2 mixed with each other at a ratio of 1:1, by the method of Example 1 above, respectively. Results thereof were shown in FIG. 3.

Figure 3:
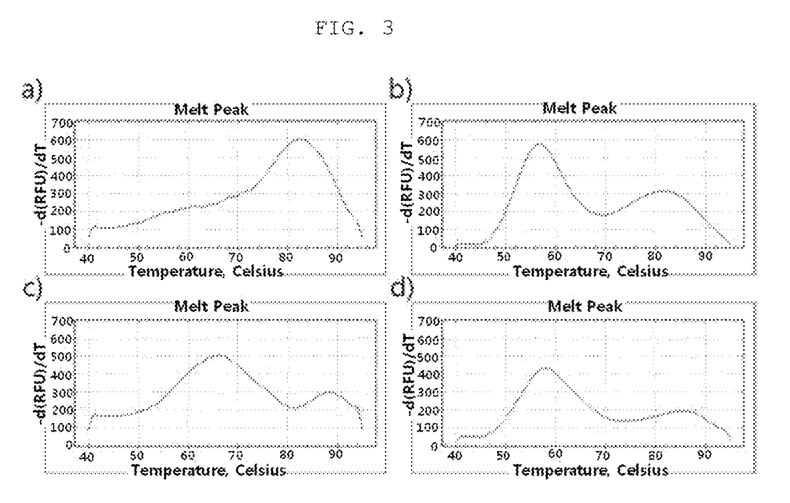
FIG. 3 shows a melting curve graph obtained by coupling the PNA probe to a heterozygous sample having a single nucleotide polymorphism;
 (a) a case of a PNA probe which is not coupled to γ-glutamic acid.
 (b) a case of a PNA probe to which two γ-glutamic acids are coupled, having two nucleotides therebetween.
 (c) a case of a PNA probe to which two γ-glutamic acids are consecutively coupled, without two nucleotides therebetween.
 (d) a case of a PNA probe to which two γ-glutamic acids are coupled, having one nucleotide therebetween.

In a case of using a PNA probe to which two γ-glutamic acids are coupled, having two nucleotides therebetween, two melting curves were the most precisely separated from each other in the heterozygous sample having the SNP.

Figure 4:
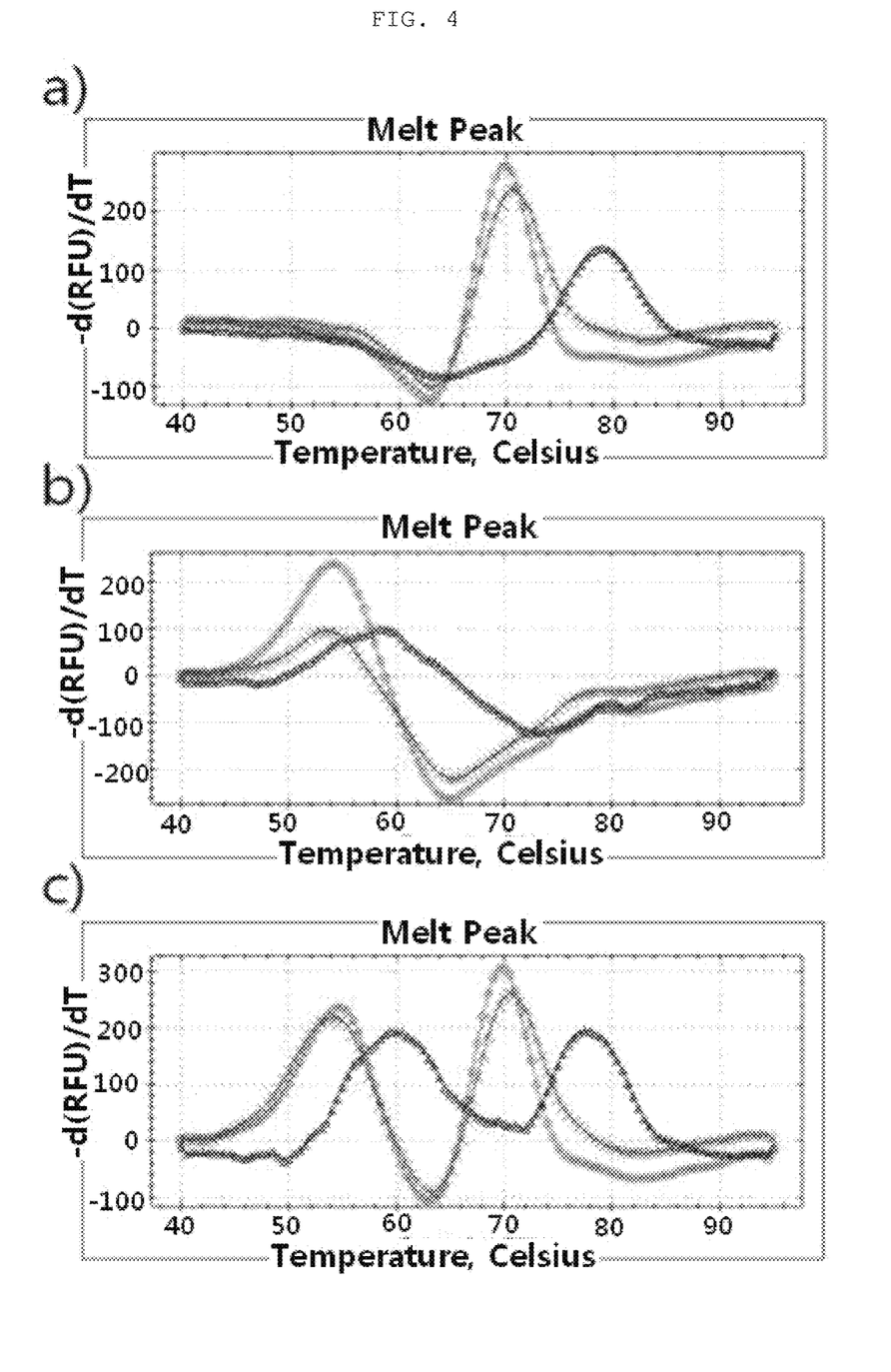

Example 4 Melting Curve Analysis of Three Different Homozygous Samples Containing Three Different PNA Probes Comprising γ-Glutamic Acid Coupled Thereto or Heterozygous Sample Including Single Nucleotide Polymorphism Example 4 was conducted by confirming whether or not Example 2 above is capable of being applied to a multiplex detection. Melting curves were analyzed by experiment using samples containing a combination of a PNA probe of SEQ ID NO: in Table 1 and a target oligomer prepared by containing a DNA oligomer of SEQ ID NO: 10 or 11 in Table 2 or by mixing both of the DNA oligomers with each other at a ratio of 1:1, a sample containing a combination of a PNA probe of SEQ ID NO: 7 in Table 1 and a target oligomer prepared by containing a DNA oligomer of SEQ ID NO: 15 or 16 in Table 2 or by mixing both of the DNA oligomers with each other at a ratio of 1:1, and a sample containing a combination of a PNA probe of SEQ ID NO: 8 in Table 1 and a target oligomer prepared by containing a DNA oligomer of SEQ ID NO: 17 or 18 in Table 2 or by mixing both of the DNA oligomers with each other at a ratio of 1:1, by the method of Example 1 above, respectively.

Results thereof were shown in FIG. 4. It was confirmed that the multiplex detection was capable of being conducted using the PNA probe comprising γ-glutamic acid coupled thereto.

Figure 5:
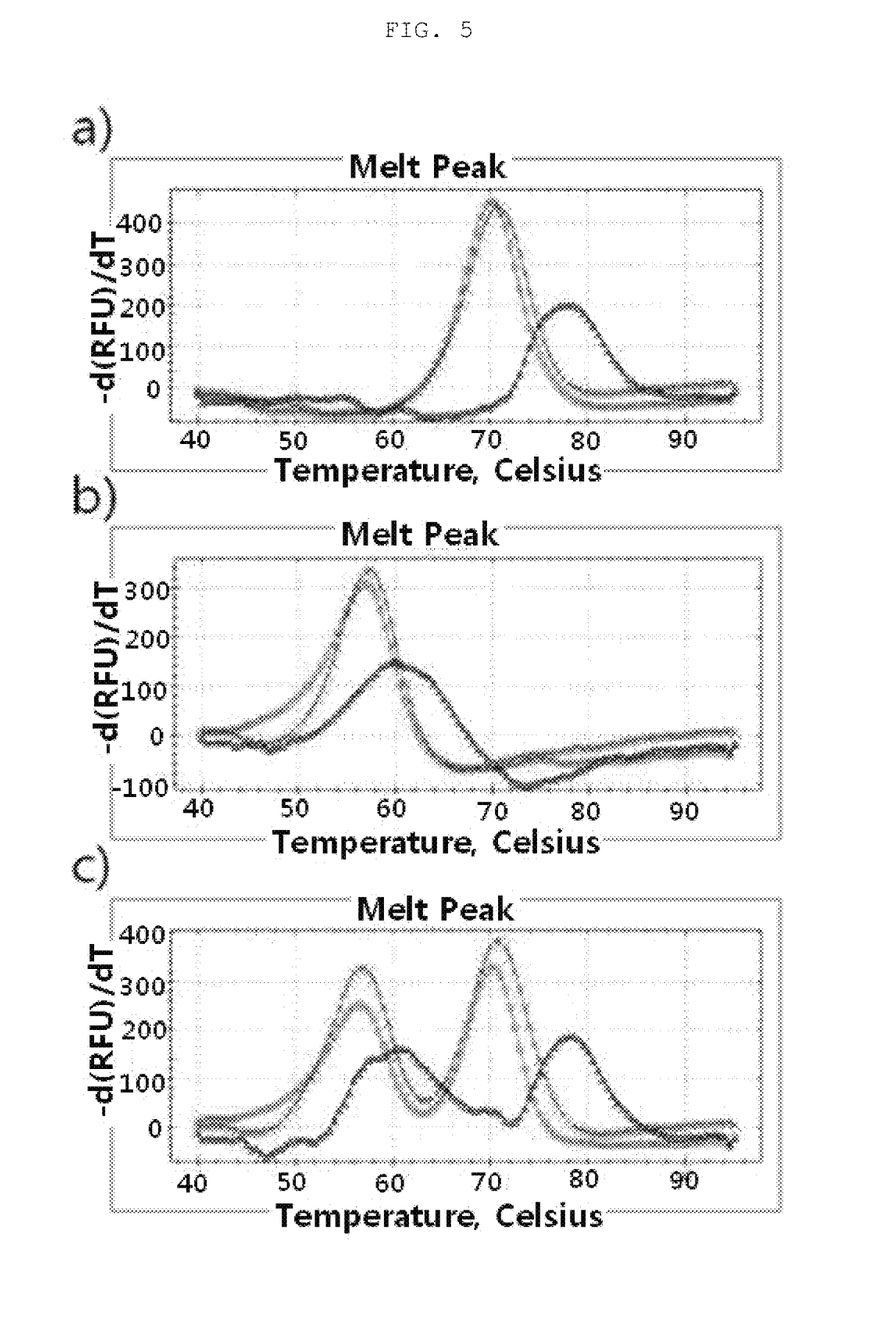
FIG. 5 shows multiplex detection in a case where three PNA probes comprising γ-glutamic acids coupled thereto are adjacent to single nucleotide polymorphism; and a black line indicates a melting curve by a PNA probe of SEQ ID NO: 2, a blue line indicates a melting curve by a PNA probe of SEQ ID NO: 7, and a red line indicates a melting curve by a PNA probe of SEQ ID NO: 8.
(a) a case of using three PNA probes comprising γ-glutamic acids coupled thereto and a DNA oligomer of SEQ ID NO: 19 in Table 2.
(b) a case of using three PNA probes comprising γ-glutamic acids coupled thereto and a DNA oligomer of SEQ ID NO: 20 in Table 2.
(c) a case of using three PNA probes comprising γ-glutamic acids coupled thereto and DNA oligomers of SEQ ID NOs: 19 and 20 in Table 2 mixed with each other at a ratio of 1:1.

Example 5 Melting Curve Analysis in Heterozygous Samples Having Adjacent Different Single Nucleotide Polymorphisms Using Three Different PNA Probes Comprising γ-Glutamic Acid Coupled Thereto Example 5 was conducted by confirming whether or not the multiplex detection ability confirmed by Example 4 above is capable of being conducted even in a case where SNPs are adjacent to each other. Melting curves were analyzed by experiment using samples containing three PNA probes of SEQ ID NOs: 2, 7, and 8 in Table 1 and a target oligomer prepared by containing a DNA oligomer of SEQ ID NO: 19 or 20 in Table 2 or by mixing both of the DNA oligomers with each other at a ratio of 1:1.

Results thereof were shown in FIG. 5. It was confirmed by using the PNA probe comprising γ-glutamic acid coupled thereto that the multiplex detection was capable of being conducted even in a case where SNPs were adjacent to each other.

Figure 6:
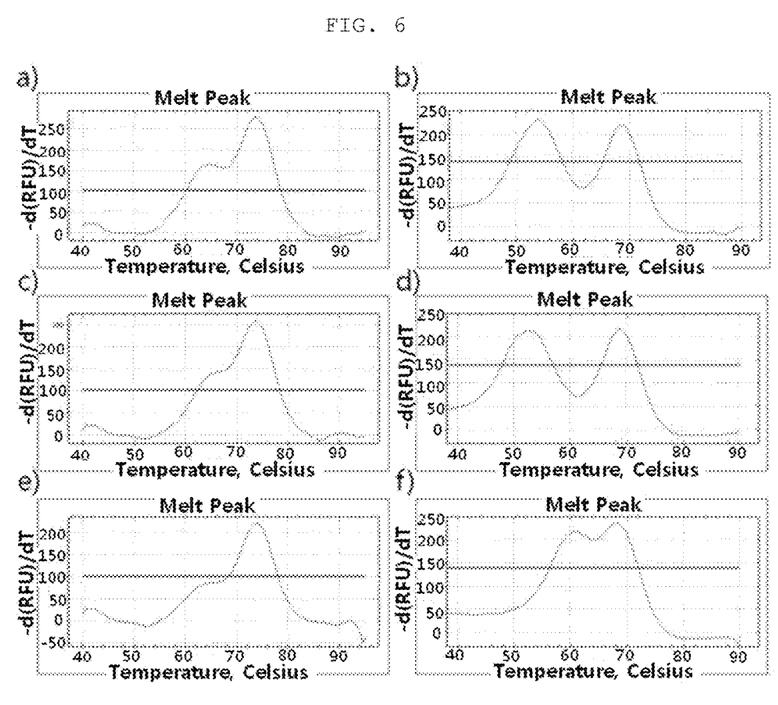

Example 6 Melting Curve Analysis in Heterozygous Samples Having Different Single Nucleotide Polymorphism Using PNA Probe Having Base Forming Mismatch at Different Position Rather than SNP Modified Position of Target DNA Introduced Thereinto In order to compare an effect of a PNA probe having a base forming a mismatch at a different position rather than a SNP modified position of the target DNA introduced thereinto, melting curves were analyzed by experiment using a sample containing a PNA probe of SEQ ID NO: 9 in Table 1 and a target oligomer prepared by mixing a DNA oligomer of SEQ ID NO: 21 with one of DNA oligomers of SEQ ID NOs: 22 to 24 in Table 2, at a ratio of 1:1, and a sample containing a PNA probe of SEQ ID NO: 9 in Table 1 and a target oligomer prepared by mixing a DNA oligomer of SEQ ID NO: 25 with one of DNA oligomers of SEQ ID NOs: 26 to 28 in Table 2, at a ratio of 1:1, by the method of Example 1 above, respectively.

Results thereof were shown in FIG. 6. It was confirmed by using the PNA probe having a base forming a mismatch at a different position rather than a SNP modified position of the target DNA introduced thereinto that two melting curves were the most precisely separated from each other in the heterozygous sample having the SNP.

The PNA fluorescent probe developed in the present invention may be used for not only the melting curve analysis method clearly described in Examples above, but also all methods capable of analyzing the target DNA using the fluorescent probe, for example, real-time PCR method; however, they are only described by way of example, and the present invention is not limited thereto. It may be appreciated by those skilled in the art that all known method may be used.

INDUSTRIAL APPLICABILITY

The backbone of the PNA probe according to the present invention may be coupled to the side chain of the amino acid having negative charges, such that the PNA probe may have a high recognition ability with respect to the target DNA and a high coupling ability to the target DNA and may be rapidly dissociated by heat. Therefore, the nucleotide polymorphism analysis method using the PNA probe containing negative charges of the present invention has advantages in that the nucleotide polymorphism analysis may be relatively easily performed even in a heterozygous sample showing two melting curve graphs, and two or more adjacent single nucleotide polymorphisms may be simultaneously analyzed. Here, the easily performed melting curve analysis is not limited to the heterozygous sample, but may be applied to all samples including a homozygous sample.

The present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

The invention claimed is:

1. A melting curve analysis method for detecting a nucleotide polymorphism of a target gene, the method comprising:
   (a) reacting a PNA probe comprising a reporter and a quencher coupled thereto with the target gene; and
   (b) analyzing melting curve for detecting the nucleotide polymorphism of the target gene, wherein the PNA probe contains two negatively charged amino acid side chains which are consecutively coupled, having two nucleotides therebetween.

2. The melting curve analysis method of claim 1, wherein the PNA probe contains intercalating fluorescent material.

3. The melting curve analysis method of claim 2, wherein the intercalating fluorescent material is not directly coupled to the probe.

4. The melting curve analysis method of claim 1, wherein the PNA probe contains at least one selected from the group consisting of amino acids, amino acid side chains, phosphoric acids, carboxylic acids, sulfonic acids, nitric acids and boric acids.

5. A nucleotide polymorphism analysis method of a target DNA, the method comprising:
   isolating a target DNA from a testing sample;
   hybridizing the target DNA with a PNA probe comprising a reporter and a quencher coupled thereto;
   obtaining a melting curve by melting a product obtained by the hybridization while changing a temperature; and
   analyzing the nucleotide polymorphism from the obtained melting curve,
   wherein the PNA probe contains two negatively charged amino acid side chains which are consecutively coupled, having two nucleotides therebetween.

6. A kit for practicing the method of claim 1, comprising: a PNA probe comprising the reporter and the quencher coupled thereto, wherein the PNA probe contains two negatively charged amino acid side chains which are consecutively coupled, having two nucleotides therebetween.

7. The kit of claim 6, wherein the kit is used for analyzing nucleotide polymorphism(s) of multiple target DNAs or a single target DNA.

* * * * *

SEQUENCE LISTING

<160> NUMBER OF SEQ ID NOS: 28

<210> SEQ ID NO 1

```
<211> LENGTH: 12
<212> TYPE: DNA
<213> ORGANISM: Artificial Sequence
<220> FEATURE:
<223> OTHER INFORMATION: synthesized sequence of DNA oligomer used in
      PNA probe 861-F71

<400> SEQUENCE: 1
caaacagctg gg                                                           12

<210> SEQ ID NO 2
<211> LENGTH: 12
<212> TYPE: DNA
<213> ORGANISM: Artificial Sequence
<220> FEATURE:
<223> OTHER INFORMATION: synthesized sequence of DNA oligomer used in
      PNA probe 861-glu2-71-65

<400> SEQUENCE: 2
caaacagctg gg                                                           12

<210> SEQ ID NO 3
<211> LENGTH: 11
<212> TYPE: DNA
<213> ORGANISM: Artificial Sequence
<220> FEATURE:
<223> OTHER INFORMATION: synthesized sequence of DNA oligomer used in
      PNA probe 858-F-78

<400> SEQUENCE: 3
ttgggcgggc c                                                            11

<210> SEQ ID NO 4
<211> LENGTH: 11
<212> TYPE: DNA
<213> ORGANISM: Artificial Sequence
<220> FEATURE:
<223> OTHER INFORMATION: synthesized sequence of DNA oligomer used in
      PNA probe 858-glu2-70

<400> SEQUENCE: 4
ttgggcgggc c                                                            11

<210> SEQ ID NO 5
<211> LENGTH: 11
<212> TYPE: DNA
<213> ORGANISM: Artificial Sequence
<220> FEATURE:
<223> OTHER INFORMATION: synthesized sequence of DNA oligomer used in
      PNA probe 858-glu270

<400> SEQUENCE: 5
ttgggcgggc c                                                            11

<210> SEQ ID NO 6
<211> LENGTH: 11
<212> TYPE: DNA
<213> ORGANISM: Artificial Sequence
<220> FEATURE:
<223> OTHER INFORMATION: synthesized sequence of DNA oligomer used in
      PNA probe 858-glu-270

<400> SEQUENCE: 6
ttgggcgggc c                                                            11

<210> SEQ ID NO 7
<211> LENGTH: 14
```

```
<212> TYPE: DNA
<213> ORGANISM: Artificial Sequence
<220> FEATURE:
<223> OTHER INFORMATION: synthesized sequence of DNA oligomer used in
      PNA probe 18-2-3

<400> SEQUENCE: 7
tagttgggat gtac                                                         14

<210> SEQ ID NO 8
<211> LENGTH: 14
<212> TYPE: DNA
<213> ORGANISM: Artificial Sequence
<220> FEATURE:
<223> OTHER INFORMATION: synthesized sequence of DNA oligomer used in
      PNA probe K13 melt

<400> SEQUENCE: 8
acgccaccag ctcc                                                         14

<210> SEQ ID NO 9
<211> LENGTH: 13
<212> TYPE: DNA
<213> ORGANISM: Artificial Sequence
<220> FEATURE:
<223> OTHER INFORMATION: synthesized sequence of DNA oligomer used in
      PNA probe K

<400> SEQUENCE: 9
gagcttggtg gcg                                                          13

<210> SEQ ID NO 10
<211> LENGTH: 30
<212> TYPE: DNA
<213> ORGANISM: Artificial Sequence
<220> FEATURE:
<223> OTHER INFORMATION: synthesized sequence of DNA oligomer 58T-61T

<400> SEQUENCE: 10
cgcacccagc tgtttggcct gcccaaaatc                                        30

<210> SEQ ID NO 11
<211> LENGTH: 30
<212> TYPE: DNA
<213> ORGANISM: Artificial Sequence
<220> FEATURE:
<223> OTHER INFORMATION: synthesized sequence of DNA oligomer 58T-61A

<400> SEQUENCE: 11
cgcacccagc agtttggcct gcccaaaatc                                        30

<210> SEQ ID NO 12
<211> LENGTH: 30
<212> TYPE: DNA
<213> ORGANISM: Artificial Sequence
<220> FEATURE:
<223> OTHER INFORMATION: synthesized sequence of DNA oligomer 58T-61G

<400> SEQUENCE: 12
cgcacccagc ggtttggcct gcccaaaatc                                        30

<210> SEQ ID NO 13
<211> LENGTH: 30
<212> TYPE: DNA
<213> ORGANISM: Artificial Sequence
<220> FEATURE:
<223> OTHER INFORMATION: synthesized sequence of DNA oligomer 58C-61C
```

```
<400> SEQUENCE: 13
cgcacccagc cgtttggcct gcccaaaatc                                    30

<210> SEQ ID NO 14
<211> LENGTH: 30
<212> TYPE: DNA
<213> ORGANISM: Artificial Sequence
<220> FEATURE:
<223> OTHER INFORMATION: synthesized sequence of DNA oligomer 58A-61C

<400> SEQUENCE: 14
cgcacccagc cgtttggcca gcccaaaatc                                    30

<210> SEQ ID NO 15
<211> LENGTH: 21
<212> TYPE: DNA
<213> ORGANISM: Artificial Sequence
<220> FEATURE:
<223> OTHER INFORMATION: synthesized sequence of DNA oligomer Tm-13-04

<400> SEQUENCE: 15
catgtacgtc ccaactacat g                                             21

<210> SEQ ID NO 16
<211> LENGTH: 21
<212> TYPE: DNA
<213> ORGANISM: Artificial Sequence
<220> FEATURE:
<223> OTHER INFORMATION: synthesized sequence of DNA oligomer Tm-13-01

<400> SEQUENCE: 16
catgtacgtc acaactacat g                                             21

<210> SEQ ID NO 17
<211> LENGTH: 26
<212> TYPE: DNA
<213> ORGANISM: Artificial Sequence
<220> FEATURE:
<223> OTHER INFORMATION: synthesized sequence of DNA oligomer 2120758-
      G(W)

<400> SEQUENCE: 17
aaggttggag atggtggcgt aggcta                                        26

<210> SEQ ID NO 18
<211> LENGTH: 26
<212> TYPE: DNA
<213> ORGANISM: Artificial Sequence
<220> FEATURE:
<223> OTHER INFORMATION: synthesized sequence of DNA oligomer 2120758-C

<400> SEQUENCE: 18
aaggttggag atgctggcgt aggcta                                        26

<210> SEQ ID NO 19
<211> LENGTH: 71
<212> TYPE: DNA
<213> ORGANISM: Artificial Sequence
<220> FEATURE:
<223> OTHER INFORMATION: synthesized sequence of DNA oligomer 3Target_W

<400> SEQUENCE: 19
cacccagctg tttggaagca tggtacgcca ctaagctcca aggaatcggt tggagatggt    60
ggcgtaggct a                                                        71
```

<210> SEQ ID NO 20
<211> LENGTH: 71
<212> TYPE: DNA
<213> ORGANISM: Artificial Sequence
<220> FEATURE:
<223> OTHER INFORMATION: synthesized sequence of DNA oligomer 3Target_M

<400> SEQUENCE: 20
cacccagcag tttggaagca tggtacgcca gtaagctcca aggaatcggt tggagatgct      60
ggcgtaggct a                                                          71

<210> SEQ ID NO 21
<211> LENGTH: 21
<212> TYPE: DNA
<213> ORGANISM: Artificial Sequence
<220> FEATURE:
<223> OTHER INFORMATION: synthesized sequence of DNA oligomer K(D)

<400> SEQUENCE: 21
catgcgccac caagctccat g                                               21

<210> SEQ ID NO 22
<211> LENGTH: 21
<212> TYPE: DNA
<213> ORGANISM: Artificial Sequence
<220> FEATURE:
<223> OTHER INFORMATION: synthesized sequence of DNA oligomer K(D)-0A

<400> SEQUENCE: 22
catgcgccac taagctccat g                                               21

<210> SEQ ID NO 23
<211> LENGTH: 21
<212> TYPE: DNA
<213> ORGANISM: Artificial Sequence
<220> FEATURE:
<223> OTHER INFORMATION: synthesized sequence of DNA oligomer K(D)-0C

<400> SEQUENCE: 23
catgcgccac gaagctccat g                                               21

<210> SEQ ID NO 24
<211> LENGTH: 21
<212> TYPE: DNA
<213> ORGANISM: Artificial Sequence
<220> FEATURE:
<223> OTHER INFORMATION: synthesized sequence of DNA oligomer K(D)-0T

<400> SEQUENCE: 24
catgcgccac aaagctccat g                                               21

<210> SEQ ID NO 25
<211> LENGTH: 21
<212> TYPE: DNA
<213> ORGANISM: Artificial Sequence
<220> FEATURE:
<223> OTHER INFORMATION: synthesized sequence of DNA oligomer K(D)-0A

<400> SEQUENCE: 25
catgcgccac taagctccat g                                               21

<210> SEQ ID NO 26
<211> LENGTH: 21
<212> TYPE: DNA

```
<213> ORGANISM: Artificial Sequence
<220> FEATURE:
<223> OTHER INFORMATION: synthesized sequence of DNA oligomer K(D)-1A

<400> SEQUENCE: 26
catgcgccaa taagctccat g                                              21

<210> SEQ ID NO 27
<211> LENGTH: 21
<212> TYPE: DNA
<213> ORGANISM: Artificial Sequence
<220> FEATURE:
<223> OTHER INFORMATION: synthesized sequence of DNA oligomer K(D)-2A

<400> SEQUENCE: 27
catgcgccag taagctccat g                                              21

<210> SEQ ID NO 28
<211> LENGTH: 21
<212> TYPE: DNA
<213> ORGANISM: Artificial Sequence
<220> FEATURE:
<223> OTHER INFORMATION: synthesized sequence of DNA oligomer K(D)-3A

<400> SEQUENCE: 28
catgcgccat taagctccat g                                              21
```